(12) United States Patent
Abbate et al.

(10) Patent No.: US 10,722,557 B2
(45) Date of Patent: Jul. 28, 2020

(54) TREATMENT OF ISCHEMIA REPERFUSION INJURY USING ALPHA-2 MACROGLOBULIN

(71) Applicant: VIRGINIA COMMONWEALTH UNIVERSITY, Richmond, VA (US)

(72) Inventors: Antonio Abbate, Richmond, VA (US); Stefano Toldo, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 16/315,684

(22) PCT Filed: Jul. 14, 2017

(86) PCT No.: PCT/US2017/042125
§ 371 (c)(1),
(2) Date: Jan. 7, 2019

(87) PCT Pub. No.: WO2018/013915
PCT Pub. Date: Jan. 18, 2018

(65) Prior Publication Data
US 2019/0142899 A1  May 16, 2019

Related U.S. Application Data

(60) Provisional application No. 62/362,122, filed on Jul. 14, 2016.

(51) Int. Cl.
*A61P 9/10* (2006.01)
*A61K 38/55* (2006.01)
*A61K 38/17* (2006.01)
*A61P 7/02* (2006.01)
*C07K 14/81* (2006.01)
*C07K 14/705* (2006.01)

(52) U.S. Cl.
CPC ............ *A61K 38/1722* (2013.01); *A61P 7/02* (2018.01); *A61P 9/10* (2018.01)

(58) Field of Classification Search
None
See application file for complete search history.

(56) References Cited

FOREIGN PATENT DOCUMENTS

WO WO-2016030316 A1 * 3/2016 ........... A61K 38/385

OTHER PUBLICATIONS

Donnelly et al, 1991. Clinica Chinnica Acta. 202: 55-64.*

* cited by examiner

*Primary Examiner* — Zachary C Howard
(74) *Attorney, Agent, or Firm* — W&C IP

(57) ABSTRACT

Methods of preventing and/or treating reperfusion injury are provided. The methods involve administering alpha-2-macroglobulin (A2MG) to a subject with ischemia in one or more tissues or organs, in order to prevent or decrease reperfusion injury when blood flow is restored to the tissues or organs (reperfusion). In some aspects, the patient who is treated has had a heart attack (e.g. acute myocardial infarction, AMI) and the ischemic tissue that is protected from reperfusion injury is heart tissue.

5 Claims, 5 Drawing Sheets

Specification includes a Sequence Listing.

Control

SVSGKPQYMVLVPSLLHTETTEKGCVLLSYLNETVTVSASLESVRGNRSLFTDLEAENDV

LHCVAFAVPKSSSNEEVMFLTVQVKGPTQEFKKRTTVMVKNEDSLVFVQTDKSIYKPGQT

VKFRVVSMDENFHPLNELIPLVYIQDPKGNRIAQWQSFQLEGGLKQFSFPLSSEPFQGSY

KVVVQKKSGGRTEHPFTVEEFVLPKFEVQVTVPKIITILEEEMNVSVCGLYTYGKPVPGH

VTVSICRKYSDASDCHGEDSQAFCEKFSGQLNSHGCFYQQVKTKVFQLKRKEYEMKLHTE

AQIQEEGTVVELTGRQSSEITRTITKLSFVKVDSHFRQGIPFFGQVRLVDGKGVPIPNKV

IFIRGNEANYYSNATTDEHGLVQFSINTTNVMGTSLTVRVNYKDRSPCYGYQWVSEEHEE

SEQ ID NO: 1

Figure 5B

MGKNKLLHPSLVLLLLVLLPTDA

SEQ ID NO: 2

TREATMENT OF ISCHEMIA REPERFUSION INJURY USING ALPHA-2 MACROGLOBULIN

CROSS-REFERENCE TO RELATED APPLICATIONS

This application claims benefit of U.S. provisional patent application 62/362,122, filed Jul. 14, 2016, the complete contents of which is hereby incorporated by reference.

SEQUENCE LISTING

This application includes as the Sequence Listing the complete contents of the accompanying text file "Sequence.txt", created Jun. 20, 2017, containing 4,171 bytes, hereby incorporated by reference.

BACKGROUND OF THE INVENTION

Field of the Invention

The invention generally relates to improved methods of preventing and/or treating reperfusion injury, such as that which occurs as a result of ischemia caused by acute myocardial infarction (AMI). In particular, the invention provides methods of preventing and/or treating reperfusion injury by administering alpha-2-macroglobulin (A2MG).

Background

Acute myocardial infarction (AMI) or "heart attack" occurs when blood flow is restricted to part of the heart muscle. It is necessary to treat heart attack victims by restoring blood flow to the entire heart as soon as possible using reperfusion therapies such as primary percutaneous coronary intervention, fibrinolytic therapy, etc. in order to limit infarct size. However, doing so unfortunately results in serious damage due to "reperfusion injury". Reperfusion (reoxygenation) injury is the tissue damage caused when blood supply returns to tissue after a period of ischemia or lack of oxygen (anoxia, hypoxia). The absence of oxygen and nutrients from blood during the ischemic period creates a condition in which the restoration of circulation results in inflammation and oxidative damage through the induction of oxidative stress rather than restoration of normal function.

Unfortunately, the development of effective therapies to reduce or prevent reperfusion injury has proven challenging. There is a critical need in the art for new therapies for the prevention and treatment of reperfusion injury, and in particular, for the prevention and treatment of reperfusion injury that results upon restoration of blood flow to ischemic heart tissue after an AMI.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

The present disclosure documents previously unrecognized tissue protective effects of alpha-2-macroglobulin (A2MG). In particular, it has been discovered that A2MG lessens damage due to reperfusion injury that would otherwise occur upon restoration of blood flow, e.g. to ischemic heart tissue after a heart attack. Thus, as described herein, A2MG is used to prevent or treat reperfusion injury e.g. after acute myocardial infarction.

It is an object of this invention to provide methods of preventing or lessening reperfusion injury in ischemic tissue in a patient in need thereof, comprising administering to the patient a therapeutically effective amount of alpha 2 macroglobulin (A2MG). In some aspects, the step of administering is performed prior to, concomitant with or after reperfusion of the ischemic tissue. In other aspects, the step of administering is performed prior to or concomitant with reperfusion of the ischemic tissue. In some aspects of the invention, the patient is an acute myocardial infarction (AMI) patient and the ischemic tissue is heart muscle. and/or preserving systolic function in an acute myocardial infarction (AMI) patient who is or will undergo reperfusion therapy, comprising administering to the patient a therapeutically effective amount of alpha-2-macroglobulin (A2M) prior to the reperfusion therapy.

The invention further provides methods of performing a surgical or medical procedure in a subject, comprising: administering A2M to the subject; stopping blood flow to a tissue or organ in the subject and performing a surgical or medical procedure with respect to the tissue or organ; and restoring blood flow to the tissue or organ. In some aspects, the step of administering A2M is performed before the step of stopping the blood flow. In other aspects, the step of administering A2M is performed concomittantly with the step of stopping the blood flow. In further aspects, the step of administering A2M is performed after the step of stopping the blood flow. In additional aspects, the tissue or organ is or is part of the heart, the brain, the kidney, the liver, the gut, or the lungs of the subject. In other aspects, the tissue or organ is the heart of the subject.

BRIEF DESCRIPTION OF THE DRAWINGS

FIGS. 5A and B. A, amino acid sequence of exemplary human A2MG; B, amino acid sequence of leader peptide of exemplary human A2MG.

DETAILED DESCRIPTION

Figure 1A:
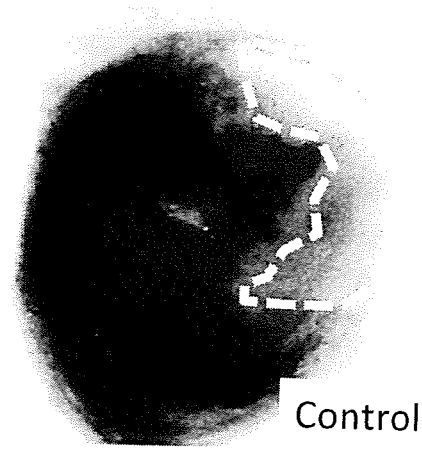
FIGS. 1A and B. Comparison of infarct size with and without A2MG administration. Infarct size was measured 24 hours following myocardial ischemia/reperfusion injury. A, control, no A2MG; B, A2MG administered following ischemia, at the time of reperfusion. Infarct size was measured using triphenyl tetrazolium chloride (TTC) and Evans blue staining.
Figure 1B:
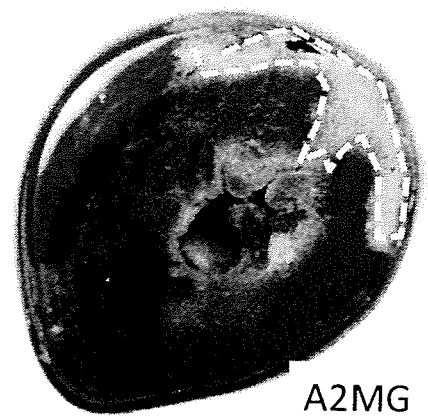

Human A2MG (also referred to a A2M, α2M, etc.), is a large 1474 amino acid homotetrameric plasma protein belonging to the protease inhibitor 139 (alpha-2-macroglobulin) family. The protein is composed of four identical disulfide-linked subunits, each of which is encoded by the A2M gene. An exemplary human A2MG amino acid sequence from which the 23 amino acid leader sequence has been removed is shown in FIG. 5A (SEQ ID NO: 1) and the leader sequence is depicted in FIG. 5B (SEQ ID NO: 2). Most A2MG is produced by the liver but the protein is also produced locally by macrophages, fibroblasts and adrenocortical cells. Previously known functions of A2MG include: inhibition of plasma proteases involved in endogenous fibrinolysis, plasmin and kallikrein; inhibition of the coagulation cascade by inhibiting thrombin; and serving as a carrier protein of growth factors and cytokines.

The present inventors have discovered that A2MG surprisingly exhibits tissue-protective effects, preventing and/or lessening reperfusion injury in ischemic tissue when blood flow is restored. For example, when A2MG is administered to a subject in whom blood flow is restored after an AMI, the amount or degree of damage to the heart muscle is significantly reduced. For example, the experimental data present herein shows that the area of the heart damaged ("infarct size") decreased by at least about 20% (up to 50%, e.g. about 20, 25, 30, 35, 40, 45 or 50%) in subjects who were treated with A2MG, in comparison to subjects who received no treatment. In addition, the level of cardiac troponin, a surrogate indicator or marker of heart damage, decreased by about 70% in treated subjects compared to untreated controls. Further, ejection volume of treated subject is maintained near normal, in contrast to untreated subjects. Thus, A2MG is an effective agent for the prevention and treatment of reperfusion injury in ischemic tissue to which a supply of blood is restored.

Accordingly, in some aspects, the invention described herein concerns the use of A2MG as a therapy for the prevention and/or treatment of reperfusion injury after an ischemic event, with AMI serving as an example of such an event.

By "ischemia" we mean an inadequate blood supply to an organ or part of the body, for example, the heart muscles.

"Reperfusion" refers to the action of restoring the flow of blood to an organ or tissue, for example, after a heart attack or stroke.

Reperfusion (reoxygenation) injury is the tissue damage caused when blood supply returns to the tissue after a period of ischemia or lack of oxygen (anoxia, hypoxia). The absence of oxygen and nutrients from blood during an ischemic period creates a condition in which the restoration of circulation results in inflammation and oxidative damage through the induction of oxidative stress rather than restoration of normal function.

Accordingly, provided herein are methods of preventing, decreasing, lessening, etc. one or more unwanted consequences of restoring the blood flow to ischemic tissue after an ischemic event, by administering a quantity of A2MG that is sufficient to prevent, decrease, lessen, etc. the unwanted consequences. The ischemic tissue may be present in an organ (e.g. part, but not all, of an organ or organ system may undergo ischemia such as one but not both lungs, one but not both lobes of the liver, etc.) or an entire organ may be subject to ischemia. In other aspects, the ischemic tissue may be present, for example, in a limb or other body part, and the ischemic tissue may comprise all or a portion of the limb, body part or organ In some aspects, the ischemia is accidental, e.g. the result of an accident, a stroke, occlusion of a blood vessel, etc. In other aspects, the ischemia is purposefully induced, e.g. before or during a medical procedure.

A2MG is advantageously commercially available in purified (e.g. substantially purified) form, being readily obtainable in large quantities from donors. The A2M described herein is generally delivered (administered) as a pharmaceutical composition. Compositions for use in the methods described herein generally include substantially purified A2MG and a pharmacologically suitable (physiologically compatible) carrier, which may be aqueous or oil-based. In some aspects, such compositions are prepared as liquid solutions or suspensions, or as solid forms such as tablets, pills, powders and the like. Solid forms suitable for solution in, or suspension in, liquids prior to administration are also contemplated (e.g. lyophilized forms), as are emulsified preparations. In some aspects, the liquid formulations are aqueous or oil-based suspensions or solutions. In some aspects, the A2MG is mixed with excipients which are pharmaceutically acceptable and compatible with the A2MG, e.g. pharmaceutically acceptable salts. Suitable excipients include, for example, water, saline, dextrose, glycerol, ethanol and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like are added. The composition of the present invention may contain any such additional ingredients so as to provide the composition in a form suitable for administration. The final amount of A2MG in the formulations varies, but is generally from about 1-99%. Still other suitable formulations for use in the present invention are found, for example in Remington's Pharmaceutical Sciences, 22nd ed. (2012; eds. Allen, Adejarem Desselle and Felton).

Some examples of materials which can serve as pharmaceutically acceptable carriers include, but are not limited to: ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

"Pharmaceutically acceptable salts" refers to the relatively non-toxic, inorganic and organic acid addition salts, and base addition salts, of compounds of the present invention. These: salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

The A2MG composition is administered by any suitable route including but not limited to: inoculation or injection (e.g. intravenous, intraperitoneal, intramuscular, subcutaneous, intraarticular, and the like) or in another suitable form. Delivery may be systemic or local. In preferred embodiments, the mode of administration is intravenous.

The subjects who are treated using the methods described herein have experienced or are experiencing at least one ischemic event in which blood flow to a tissue, organ, limb, etc. has been reduced or eliminated, and in whom the blood flow to the tissue, organ, limb, etc. is to be restored. The onset of ischemia may be deliberate (for a particular purpose) and controlled e.g. through external manipulation such as in surgical or medical procedures; or may be inadvertent, e.g. caused by an accident or disease or other ischemia inducing condition. Exemplary ischemic events include but are not limited to: birth asphyxia in newborn infants; brain ischemia resulting from stroke or brain trauma; brain failure due to cardiac arrest; repeated bouts of ischemia as observed in the formation and failure to heal of chronic wounds such as pressure sores and diabetic foot ulcers; various procedures in cardiac surgery such as aortic cross-clamping and the use of Resuscitative Endovascular Balloon Occlusion of the Aorta (REBOA) devices; traumatic vessel disruption; tourniquet application (e.g. pneumatic, surgical tourniquets and emergency field tourniquets); shock; resuscitation post cardiac arrest; limb ischemia; intestinal ischemia; retinal ischemia etc. The ischemic tissue that is treated, preferably before or at the time of restoring blood flow, may be from any tissue or organ of the body, including but not limited to cardiac, brain, kidney, bowel, limb, digit and cutaneous tissue. While it is generally preferred to deliver the A2MG prior to or at the time of reperfusion, benefits may also result from administration after reperfusion.

In some aspects, the subjects who are treated using the methods described herein are patients with some type of heart disease that results in and/or is characterized by ischemia. Exemplary heart diseases include but are not limited to: unstable angina, acute myocardial infarction (AMI), multivessel coronary artery disease (CAD), ST-segment-elevation MI (STEMI), cardiogenic shock, acute heart failure, acute cardiomyopathy ventricular arrhythmias, etc. In particular, the population that is served by the invention includes patients who have had or who are experiencing a heart attack, and who require or are undergoing a treatment to restore blood flow to ischemic areas of the heart. Examples of such procedures include but are not limited to acute and non-acute percutaneous coronary intervention or "PCI" procedures such as angioplasty with or without implantation of stent; thrombolysis by injection of a clot-dissolving agent; coronary artery bypass graft surgery (CABG); electrical therapy, etc.

The subjects that are treated according to the methods described herein are typically mammals, usually humans. However, veterinary applications of these methods are also encompassed, especially for companion or prized domesticate animals that are subject to ischemia, of any type (e.g. ischemia of heart tissue induced by surgery or trauma) and likely to undergo reperfusion. In some aspects, a species-specific A2MG may be used for such treatment.

Typically, an infusion of A2MG is started before, during, or after (preferably immediately before or during) the therapies or procedures used to reperfuse the ischemic myocardium. A2MG is given at a dose ranging from about 1-1000 mg/kg, e.g. about 5 to 500 mg/kg, and usually from about 10 to about 300 mg/kg without any organ toxicity or side effects. For example, amounts of about 10, 20, 30, 40, 50, 60, 70, 80, 90, 100, 125, 150, 175, 200, 225, 250, 275 or 300 mg/kg may be employed. A2MG is typically present at high levels in circulation (e.g. about 200-400 mg/100 ml), and the dose administered as described herein increases the amount of A2MG in the circulatory system above that which occurs naturally, e.g. by at least about 1-10% or more, e.g. to at least about 450, or 500 mg/100 ml or more, e.g. about 500, 600, 700, 800, 900 or 1000 mg/100 ml. Generally, the infusion occurs intravenously (peripheral or central intravenous administration) over a duration of 1 to 60 minutes, e.g. 1, 5, 10, 20, 30, 40, 50 or 60 minutes. In some aspects, the patient requires monitoring for signs of reaction to blood products or components of the carrier (i.e. anaphylaxis) for approximately 1 hour after infusion. However, in some advantageous aspects, no laboratory tests are needed to monitor the activity or toxicity of A2MG itself, which is already present at high levels in the circulatory system. The step of administering may be repeated one or more times, as necessary or desirable, e.g. administration may be 1, 2, 4, 6 or more times per day, and in fact, may be more or less continuous (e.g. via an IV line) over a period of several (e.g. 8-24 or even 48 hours) or even for several days (e.g. 1-7 days) after reperfusion. Administration may also be begun "early" to prepare the patient for reperfusion, if there is time before a procedure (e.g. several hours or even a few days early).

In some aspects, administration of A2MG completely eliminates injury that would otherwise occur following reperfusion. However, much benefit can accrue even if such damage or injury is not completely prevented, but is lessened (decreased, lowered) compared to subjects who do not receive A2MG. For example, for AMI patients, while damage may not be completely eliminated: the infarct size may be decreased significantly (e.g. at least about 10, 20, 30, 40, 50, 60, 70, 80 or 90% or more, compared to untreated individuals); and/or the level of one or more surrogate markers of heart damage such as troponin may be decreased significantly (e.g. at least about 10, 20, 30, 40, 50, 60, 70, 80 or 90% or more compared to untreated individuals); and/or other markers of heart health e.g. ejection fraction, may be maintained at a higher level (e.g. at least about 50, 60, 70, 80 or 90% or more of the normal value, compared to untreated individuals, who suffer a greater loss).

In further aspects, A2MG is administered in conjunction with (together with) one or more other therapies for the prevention or treatment of reperfusion injury, including but not limited to, for example: hydrogen sulfide, cyclosporine, TRO40303, mesenchymal stem cells, superoxide dismutase, metformin, hypothermia treatments, etc.

With respect to heart disease in particular, in some aspects, the A2MG is administered in conjunction with (together with) one or more other therapies typically used for the treatment of heart disease, heart attack, etc., such as, for example, nitroglycerin, blood thinners such as warfarin, angiotensin converting enzyme (ACE) inhibitors, antiarrhythmics, antiplatelet agents, aspirin, beta-blockers, calcium channel blockers, thrombolytic agents, diuretics, digoxin, etc. When A2MG is administered "with" one or more other agents, it may be included in the same composition, or may be administered in a separate composition but at the same, or at overlapping times, etc. so that both or all agents in the combination are present in the patient's circulatory system at the same time, for at least a portion of the treatment period.

In some aspects, A2MG is not administered with corticotropin releasing hormone (CRH). In other aspects, A2MG is not administered with tissue plasminogen activator. In further aspects, the A2MG is not administered with a substance that upregulates expression of a nucleic acid encoding A2MG, and, in subjects treated as described herein, levels of A2MG in the blood are not increased by administering a substance that upregulates expression of a nucleic acid encoding A2MG.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Example 1

Data was obtained using the experimental model of acute myocardial ischemia in the mouse.

Briefly, adult male ICR mice were used for this experiment. The mice were sedated with pentobarbital and received analgesia with buprenorphine, then were intubated with a cannula in the trachea, and attached to a ventilator. The chest was opened under surgical microscopy view and the left coronary artery was identified after opening of the chest cavity and peeling of the pericardium. The artery was ligated with a 7.0 silk sutures for 30 minutes, during which time the mid and apical anterior wall of the myocardium appeared pale.

After 30 minutes, the ligation was released and reperfusion of the myocardium was visually assessed by return of reddish color in the area that was previously pale. Treatment with A2MG (derived from human plasma, MyBioSource, Inc., San Diego, Calif. or Molecular Innovation, Novi, Mich.) 3, 10, 30 or 60 mg/kg was given intraperitoneally to the experimental mice right after the reperfusion was achieved. The chest cavity was closed, and the mouse was allowed to recover, detached from the ventilator and followed until recovery. Mice were given food and water ad libitum, and reassessed the next day.

After 24 hours, the mice were sedated and the left ventricular fractional shortening was assessed using transthoracic M-mode echocardiography to measure the myocardial function and damage. Subsequently, the abdomen and chest were reopened and the heart stained. A triphenyl tetrazolium chloride (TTC) solution was injected directly into the left ventricle while the aortic outflow was temporarily obstructed so as to distribute the TTC stain to the entire heart. After repeat ligation of the left coronary, Evans blue dye was infused retrogradely in the aorta to stain the non-risk myocardial area. The heart was then collected, frozen, and cut in 5-7 transverse sections. Planimetry was used to measure the areas of blue myocardium (non-risk), red myocardium (viable risk area) and white myocardium (non-viable myocardium in the risk area). Infarct size was calculated as non-viable myocardium/(entire myocardial area−non-risk area)×100. In addition, a plasma sample was taken and troponin I levels were assayed through ELISA as a surrogate of infarct size.

Results

Figure 2A:
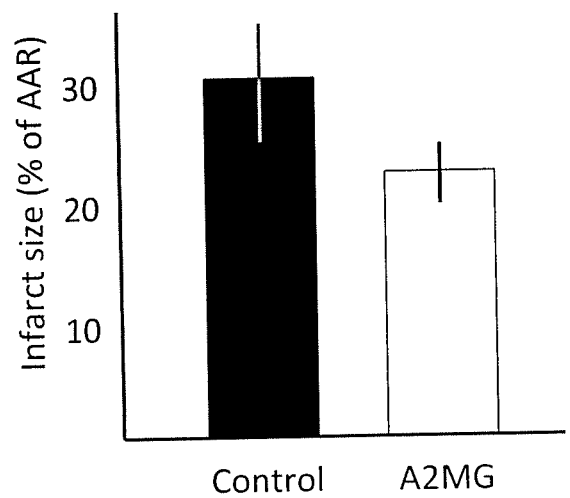
FIGS. 2A and B. Comparison of infarct size and cardiac troponin with and without A2MG administration. A, infarct size; B, cardiac troponin.
Figure 2B:
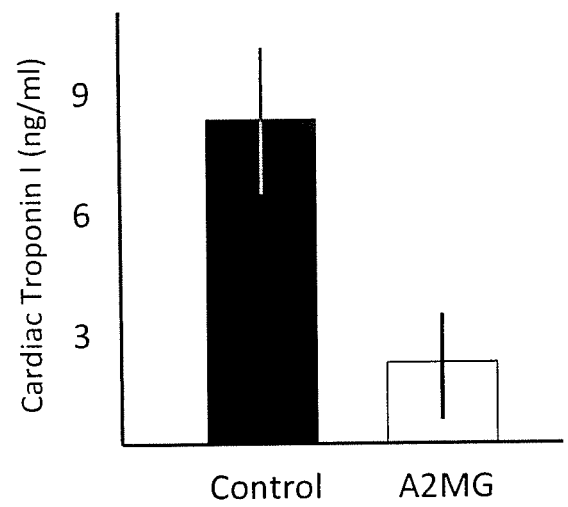

The results showed that administration of A2MG resulted in a significantly smaller infarct size (FIGS. 1A and B). In addition, A2MG administration resulted in significantly lower plasma levels of troponin I, a surrogate of infarct size (FIGS. 2A and B).

Example 2

Additional experiments were completed to measure the effects of alpha-2 macroglobulin (A2MG) at lower doses, with the aim of determining the lowest yet most effective dose to reduce infarct size and preserve the ejection fraction following acute myocardial infarction. The doses tested were 30, 10 and 3 mg/kg, which were added to the study to build a dose response curve together with the dose of 60 mg/kg used in the pilot study.

Briefly, adult male CD1 mice were anesthetized, intubated and underwent 30 minutes of coronary artery ligation followed by 24 hours of reperfusion. The mice were randomized to the different doses of A2MG, which were administered at the moment of reperfusion only after assessing successful reopening of the coronary artery. A2MG was dissolved at the desired concentration in aqueous NaCl 0.9%, in a volume of 0.1 ml. Cardiac function was measured non-invasively by transthoracic echocardiography. Infarct size was measured at pathology using triphenyl-tetrazolium-chloride staining for viable myocardium and phtalo-blue perfusion for non-risk myocardium, and expressed as percent of myocardium at risk. The results were compared to the control group of mice that were treated with a matching volume of NaCl 0.9% solution as a single dose at the time of reperfusion.

Results

Figure 3A:
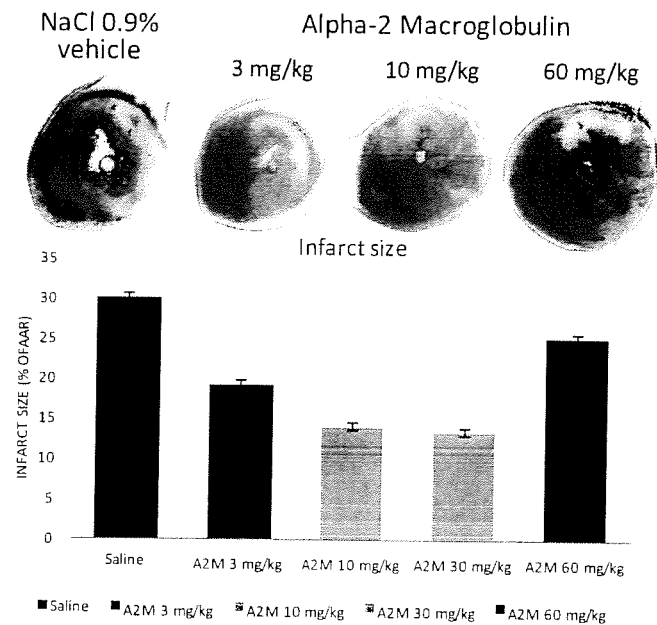
FIGS. 3A and B. Dose response characterization of infarct size and systolic function 24 hours following myocardial ischemia/reperfusion injury. A, infarct size in mice treated with the vehicle control, or 3, 10, 30 or 60 mg/kg of A2MG; B, fractional shortening of the left ventricle of mice treated with the control vehicle or 3, 10, 30 or 60 mg/kg of A2MG.
Figure 3B:
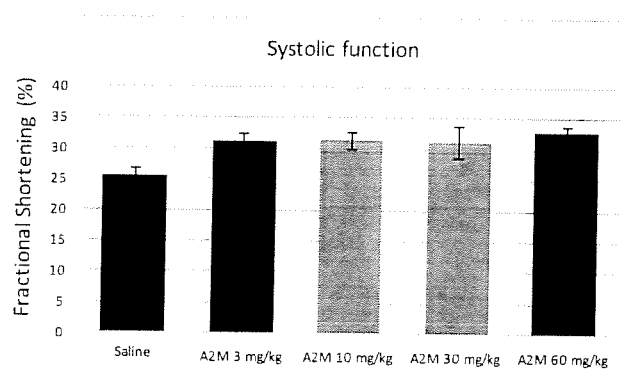
Figure 4:
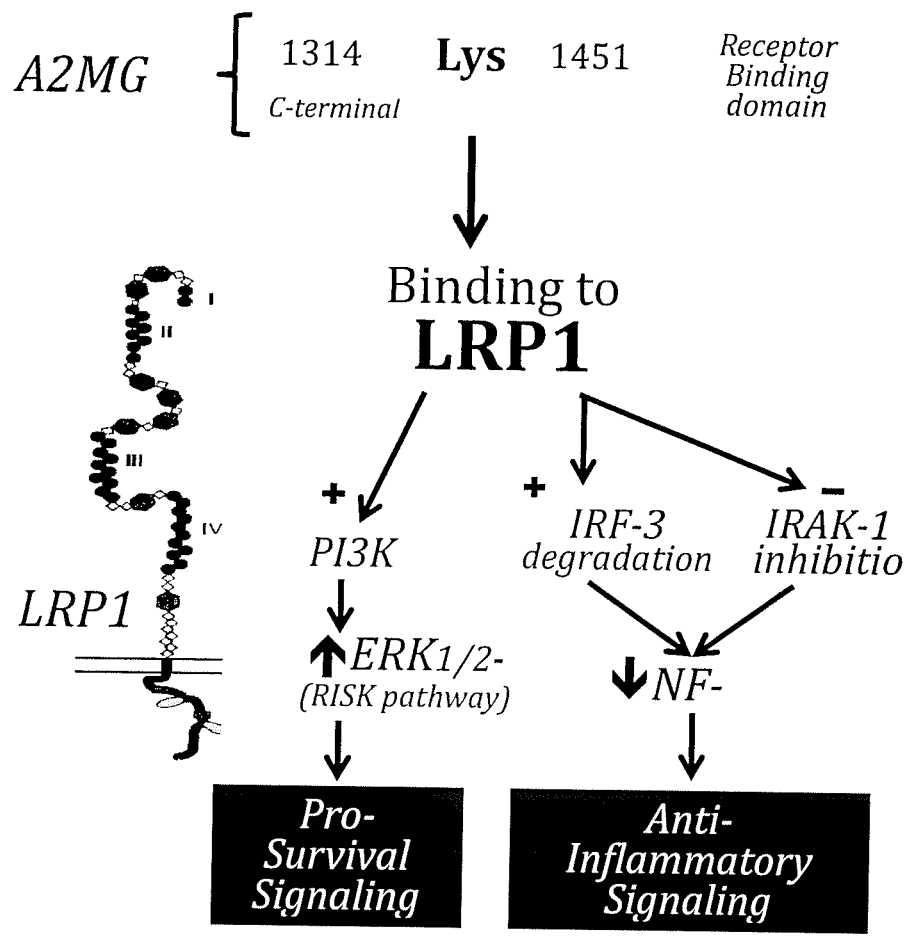
FIG. 4. Schematic representation of A2MG binding to the LRP1 membrane receptor.

The administration of A2MG at any dose tested provided a significant reduction in infarct size, compared with vehicle (FIGS. 3A and B). The dose-response curve showed a U-shaped response with a greater response for the intermediate doses of 10 and 30 mg/kg (FIG. 3A). A2MG significantly preserved systolic function measured as left ventricular fractional shortening (FS) at all the doses tested (FIG. 3B). Without being bound by theory, it is believed that A2MG binding induces an anti-inflammatory and cytoprotective signal (FIG. 4).

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of lessening reperfusion injury in ischemic tissue by inducing an anti-inflammatory and cytoprotective signal in a patient in need thereof, comprising administering to the patient a therapeutically effective amount of alpha 2 macroglobulin (A2MG), wherein said therapeutically effective amount of A2MG is sufficient to bind a LRP1 membrane receptor and binds said LRP1 membrane receptor so as to produce anti-inflammatory and cytoprotective signaling in at least one cell in said ischemic tissue.

2. The method of claim 1, wherein the step of administering is performed prior to, concomitant with or after reperfusion of the ischemic tissue.

3. The method of claim 2, wherein the step of administering is performed prior to or concomitant with reperfusion of the ischemic tissue.

4. The method of claim 1, wherein the patient is an acute myocardial infarction (AMI) patient and the ischemic tissue is heart muscle.

5. The method of claim 1, wherein said A2MG is a solution or suspension of substantially purified A2MG in a pharmaceutically acceptable carrier.

* * * * *

SEQUENCE LISTING

```
<160> NUMBER OF SEQ ID NOS: 2

<210> SEQ ID NO 1
<211> LENGTH: 420
<212> TYPE: PRT
<213> ORGANISM: Homo sapiens

<400> SEQUENCE: 1

Ser Val Ser Gly Lys Pro Gln Tyr Met Val Leu Val Pro Ser Leu Leu
1               5                   10                  15

His Thr Glu Thr Thr Glu Lys Gly Cys Val Leu Leu Ser Tyr Leu Asn
            20                  25                  30

Glu Thr Val Thr Val Ser Ala Ser Leu Glu Ser Val Arg Gly Asn Arg
        35                  40                  45

Ser Leu Phe Thr Asp Leu Glu Ala Glu Asn Asp Val Leu His Cys Val
    50                  55                  60

Ala Phe Ala Val Pro Lys Ser Ser Ser Asn Glu Val Met Phe Leu
65                  70                  75                  80

Thr Val Gln Val Lys Gly Pro Thr Gln Glu Phe Lys Lys Arg Thr Thr
                85                  90                  95

Val Met Val Lys Asn Glu Asp Ser Leu Val Phe Val Gln Thr Asp Lys
            100                 105                 110

Ser Ile Tyr Lys Pro Gly Gln Thr Val Lys Phe Arg Val Val Ser Met
        115                 120                 125
```

```
Asp Glu Asn Phe His Pro Leu Asn Glu Leu Ile Pro Leu Val Tyr Ile
        130                 135                 140

Gln Asp Pro Lys Gly Asn Arg Ile Ala Gln Trp Gln Ser Phe Gln Leu
145                 150                 155                 160

Glu Gly Gly Leu Lys Gln Phe Ser Phe Pro Leu Ser Ser Glu Pro Phe
                165                 170                 175

Gln Gly Ser Tyr Lys Val Val Gln Lys Ser Gly Gly Arg Thr
                180                 185                 190

Glu His Pro Phe Thr Val Glu Glu Phe Val Leu Pro Lys Phe Glu Val
                195                 200                 205

Gln Val Thr Val Pro Lys Ile Ile Thr Ile Leu Glu Glu Met Asn
        210                 215                 220

Val Ser Val Cys Gly Leu Tyr Thr Tyr Gly Lys Pro Val Pro Gly His
225                 230                 235                 240

Val Thr Val Ser Ile Cys Arg Lys Tyr Ser Asp Ala Ser Asp Cys His
                245                 250                 255

Gly Glu Asp Ser Gln Ala Phe Cys Glu Lys Phe Ser Gly Gln Leu Asn
                260                 265                 270

Ser His Gly Cys Phe Tyr Gln Gln Val Lys Thr Lys Val Phe Gln Leu
                275                 280                 285

Lys Arg Lys Glu Tyr Glu Met Lys Leu His Thr Glu Ala Gln Ile Gln
                290                 295                 300

Glu Glu Gly Thr Val Val Glu Leu Thr Gly Arg Gln Ser Ser Glu Ile
305                 310                 315                 320

Thr Arg Thr Ile Thr Lys Leu Ser Phe Val Lys Val Asp Ser His Phe
                325                 330                 335

Arg Gln Gly Ile Pro Phe Phe Gly Gln Val Arg Leu Val Asp Gly Lys
                340                 345                 350

Gly Val Pro Ile Pro Asn Lys Val Ile Phe Ile Arg Gly Asn Glu Ala
                355                 360                 365

Asn Tyr Tyr Ser Asn Ala Thr Thr Asp Glu His Gly Leu Val Gln Phe
                370                 375                 380

Ser Ile Asn Thr Thr Asn Val Met Gly Thr Ser Leu Thr Val Arg Val
385                 390                 395                 400

Asn Tyr Lys Asp Arg Ser Pro Cys Tyr Gly Tyr Gln Trp Val Ser Glu
                405                 410                 415

Glu His Glu Glu
        420

<210> SEQ ID NO 2
<211> LENGTH: 23
<212> TYPE: PRT
<213> ORGANISM: Homo sapiens

<400> SEQUENCE: 2

Met Gly Lys Asn Lys Leu Leu His Pro Ser Leu Val Leu Leu Leu Leu
1               5                   10                  15

Val Leu Leu Pro Thr Asp Ala
            20
```